United States Patent
Mojaver

(10) Patent No.: US 12,403,025 B1
(45) Date of Patent: Sep. 2, 2025

(54) ORAL DEVICE TO INHIBIT MASTICATION AND INGESTION OF SOLID FOOD

(71) Applicant: Mahnaz Nina Mojaver, San Diego, CA (US)

(72) Inventor: Mahnaz Nina Mojaver, San Diego, CA (US)

(73) Assignee: Mahnaz Nina Mojaver, San Diego, CA (US)

( * ) Notice: Subject to any disclaimer, the term of this patent is extended or adjusted under 35 U.S.C. 154(b) by 0 days.

(21) Appl. No.: 18/668,059

(22) Filed: May 17, 2024

(51) Int. Cl.
*A61F 5/00* (2006.01)
*A61C 7/36* (2006.01)
*B29C 64/386* (2017.01)

(52) U.S. Cl.
CPC .......... *A61F 5/0006* (2013.01); *A61F 5/0089* (2013.01)

(58) Field of Classification Search
CPC ..... A61C 13/34; A61C 13/20; A61C 13/0019; A61C 7/08; A61C 7/36; A61F 5/0006; A61F 5/0089; A61F 5/56; A61F 5/566; A61F 2005/563; A63B 71/085; A63B 2071/086; A63B 2071/088; B29C 64/386; B29C 64/106; B33Y 50/00; B33Y 50/02; B33Y 10/00
See application file for complete search history.

(56) References Cited

U.S. PATENT DOCUMENTS

| | | | |
|---|---|---|---|
| 4,471,771 A | 9/1984 | Brown et al. | |
| 4,738,259 A | 4/1988 | Brown et al. | |
| 11,116,652 B2 | 9/2021 | Mojaver | |
| 11,759,344 B2 | 9/2023 | Mojaver | |
| 2003/0075186 A1 | 4/2003 | Florman | |
| 2018/0360567 A1* | 12/2018 | Xue | G06T 7/10 |
| 2022/0313409 A1* | 10/2022 | Pai | A46B 13/06 |

* cited by examiner

*Primary Examiner* — Camtu T Nguyen
(74) *Attorney, Agent, or Firm* — Akerman LLP

(57) ABSTRACT

The present invention is oral device that inhibits mastication and ingestion of solid food while minimizing intrusiveness and discomfort in other oral activities. This device is ideal for individuals following an all-liquid diet without relying on willpower alone. The oral device allows a full range of motion of the jaw and the wearer keeps the ability to open and close the mouth, allowing all oral functions other than chewing and swallowing solid food. In various embodiments of the invention, the oral device comprises a set of retainers worn over teeth or retainer bars bonded to, or integrated as part of the retainers. A set of flexible mastication barriers coupled to the retainers or retainer bars and extending from mandible to the maxilla on the lingual side of the mouth inhibit the movement of solid food to the occlusal surfaces of the posterior teeth for chewing. An artificial intelligence platform is implemented to improve fabrication of the oral device and predict and eliminate undercuts in the retainers or retainer bars.

6 Claims, 15 Drawing Sheets

ORAL DEVICE TO INHIBIT MASTICATION AND INGESTION OF SOLID FOOD

BACKGROUND OF THE INVENTION

1. Field of Invention

The present invention relates to oral devices that inhibit a wearer's ability to masticate and ingest solid food while allowing natural jaw movement without discomfort.

2. Description of Related Art

An all-liquid diet has proven to be an effective diet for weight loss. This diet may be based upon any appropriate liquid or combination of liquids, such that dieters consume all the essential nutrients for a healthy lifestyle without ingredients that contribute to weight gain or prevent weight loss. Many solids, including fast food, commercially processed food, and food with added sugar, have been linked to weight gain, obesity, and health problems. A challenging aspect of maintaining a liquid diet is the continuous self-control needed to prevent consuming these solid foods.

Mastication, i.e., chewing food into smaller particles, is essential for ingesting solid foods. Outside of wiring one's mouth shut, which increases the risk of choking and dental problems, attempts have been made to block solid foods from being swallowed while allowing tongue and jaw movement for talking. For example, U.S. Pat. No. 4,471,771 teaches a sieve-like blocking means secured to a user's upper teeth and pivots between closed and open positions. In its closed position, liquids and finely ground foods may freely pass through, but solid foods may not. However, during regurgitation, matter expelled from the stomach forces the blocking means to an open position, allowing the regurgitated matter to exit the mouth. Such a moving oral device is awkward and uncomfortable to wear, permits food to be trapped in the mouth, and does not inhibit the chewing of solid foods.

U.S. Pat. No. 4,738,259 discloses an outwardly projecting flange attached to a support collar to make chewing more difficult. Yet, this device does not entirely block food from contacting the tooth surfaces responsible for chewing and grinding solid food. In addition, the device is cumbersome and uncomfortable to wear and can be removed by the wearer.

United States Patent Application Publication No. 2003/0075186 provides a device that restricts the opening of the wearer's mouth to slow the ingestion of food and purportedly increase satiety. However, it does not prevent the chewing and swallowing of solid foods. Moreover, a wearer would likely find the device impractical.

Prior art devices like those above attach to the user's teeth in a manner that can cause teeth to shift, potentially resulting in a super eruption of teeth from the dental bones and increasing the likelihood of tooth damage or loss.

A need exists for an oral weight control device that affixes to the teeth in a manner that does not cause the teeth to shift and does not impede tongue and jaw movement, thereby allowing the wearer to speak and otherwise open and close their mouth without restriction, while still inhibiting the chewing and swallowing of solid foods. Further, there is a need for such a device that minimizes the effect on the user, including discomfort and the difficulty of maintaining proper dental hygiene with such a device in place.

The present inventor's U.S. Pat. Nos. 11,116,652 and 11,759,344, the entire disclosures of which are incorporated herein by reference, teach a dental appliance that utilizes an upper retainer and a lower retainer with left and right flexible food barriers on the lingual side of the teeth to prevent food that a user may attempt to masticate from being passed to the tongue to ingest. The dental appliance is comfortable and allows a full range of jaw motion. The wearer can perform all the mouth functions besides chewing and swallowing solid food. The present invention builds upon and expands the scope of the inventor's technology in several novel and non-obvious ways, as described below.

SUMMARY OF THE INVENTION

The present invention provides an oral device that inhibits chewing and ingesting solid food while minimizing intrusiveness and discomfort in other oral activities. This device is ideal for individuals following an all-liquid diet without relying on willpower alone. The oral device allows a full range of motion of the jaw, and the wearer keeps the ability to open and close the mouth, allowing all oral functions other than chewing and swallowing solid food. In various embodiments of the invention, the oral device comprises a left and right set of retainer bars bonded to, or integrated as part of a retainer worn over, posterior teeth (molars and premolars/canines) to inhibit the movement of solid food to the occlusal surfaces of the posterior teeth for chewing. Each set of retainer bars is coupled to a flexible mastication barrier, extending from the mandible to the maxilla on the lingual side. Artificial intelligence is implemented to improve the fabrication of the oral device and predict and eliminate undercuts.

In an embodiment of the invention, an oral device comprises a first mandibular retainer bar comprising a teeth contact surface contoured to a lingual surface of one or more mandibular posterior teeth on a first side of a recipient's mouth, a first maxillary retainer bar comprising a teeth contact surface contoured to a lingual surface of one or more maxillary posterior teeth on the first side of the recipient's mouth, and a first mastication barrier configured to be connected to the first mandibular retainer bar and the first maxillary retainer bar. The first mastication barrier comprises a first tab at a first edge and a second tab at a second edge opposite the first edge. The first mandibular retainer bar comprises a slot configured to receive the first tab of the first mastication barrier. The first maxillary retainer bar comprises a slot configured to receive the second tab of the first mastication barrier. The first tab and the second tab may be hollow cylinders. The first mandibular retainer bar comprises a handle arm configured to receive the first tab of the first mastication barrier. The first maxillary retainer bar comprises a handle arm configured to receive the second tab of the first mastication barrier. The first mandibular retainer bar may comprise a first array of hooks, and the first maxillary retainer bar comprises a second array of hooks. The first mastication barrier may comprise a first array of loops at a first edge and a second array of loops at a second edge opposite the first edge. The second mandibular retainer bar comprises a teeth contact surface contoured to a lingual surface of one or more mandibular posterior teeth on a second side of the recipient's mouth, wherein the first side of the recipient's mouth is a left side and the second side of the recipient's mouth is a right side, a second maxillary retainer bar comprises a teeth contact surface contoured to a lingual surface of one or more maxillary posterior teeth on the second side of the recipient's mouth. A second mastication barrier is configured to connect to the second mandibular and the second maxillary retainer bars. The oral device may further comprise a first removable jig comprising a jig check including a surface contoured to a portion of the lingual surface, an occlusal surface, and a portion of a buccal surface of the one or more mandibular posterior teeth on the first side of the recipient's mouth, and a retainer holder including an arm configured to place the first mandibular retainer in a predetermined position adjacent to the lingual surface of the one or more mandibular posterior teeth on the first side of a recipient's mouth when the jig check is fitted over the lingual surface, an occlusal surface, and a portion of a buccal surface of the one or more mandibular posterior teeth on the first side of the recipient's mouth.

In another embodiment of the invention, a method for inhibiting mastication of solid food comprises the steps of bonding a first mandibular retainer bar to a lingual surface of one or more mandibular posterior teeth on a first side of a recipient's mouth, bonding a first maxillary retainer bar to a lingual surface of one or more maxillary posterior teeth on the first side of a recipient's mouth, and connecting a first mastication barrier to the first mandibular retainer bar and the second maxillary retainer bar. The step of connecting comprises inserting a first tab of the first mastication barrier into a slot of the first mandibular retainer bar and inserting a second tab of the first mastication barrier into a slot of the first maxillary retainer bar. The may further comprise the steps of bonding a second mandibular retainer bar to a lingual surface of one or more mandibular posterior teeth on a second side of the recipient's mouth, wherein the first side of the recipient's mouth is a left side and the second side of the recipient's mouth is a right side, bonding a second maxillary retainer bar to a lingual surface of one or more maxillary posterior teeth on the second side of the recipient's mouth, and connecting a second mastication barrier configured to the second mandibular retainer bar and the second maxillary retainer bar. The step of bonding the first mandibular retainer bar to the lingual surface of the one or more mandibular posterior teeth on the first side of the recipient's mouth comprises placing a jig check over a portion of the lingual surface, an occlusal surface, and a portion of a buccal surface of the one or more mandibular posterior teeth on the first side of a recipient's mouth.

In another embodiment of the invention, an oral device comprises a jig check including a surface contoured to a portion of a lingual surface, an occlusal surface, and a portion of a buccal surface of one or more posterior teeth, and a retainer holder including an arm configured to place a retainer bar in a predetermined position adjacent to the lingual surface of the one or more posterior teeth when the jig check is placed over the portion of the lingual surface, the occlusal surface, and the portion of the buccal surface of the one or more posterior teeth.

In yet another embodiment of the invention, an oral device comprises: a first retainer configured to fit over a recipient's mandibular teeth, wherein the first retainer comprises a first retainer bar adjacent to a lingual surface of one or more mandibular posterior teeth on a first side of the recipient's mouth, a second retainer bar adjacent to a lingual surface of one or more mandibular posterior teeth on a second side of the recipient's mouth, a second retainer configured to fit over the recipient's maxillary teeth, wherein the second retainer comprises a first retainer bar adjacent to a lingual surface of one or more maxillary posterior teeth on the first side of the recipient's mouth, a second retainer bar adjacent to a lingual surface of one or more maxillary posterior teeth on the second side of the recipient's mouth, a first mastication barrier configured to be connected to the first retainer bar of the first retainer and the first retainer bar of the second retainer, and a second mastication barrier configured to be connected to the second retainer bar of the first retainer and the second retainer bar of the second retainer. The first mastication barrier comprises a first tab at a first edge and a second tab at a second edge opposite the first edge. The first mandibular retainer bar comprises a slot configured to receive the first tab of the first mastication barrier. The first maxillary retainer bar comprises a slot configured to receive the second tab of the first mastication barrier.

In another embodiment of the invention, a method of creating a retainer comprises the steps of receiving a dental scan representing a dental structure; processing the dental scan using an artificial intelligence model, wherein the artificial intelligence model is trained on a dataset comprising a plurality of dental scans representing unique dental structures; and generating a digital model of a dental retainer based on the processed dental scan, wherein the digital model is optimized, through the artificial intelligence model, for the dental structure represented in the dental scan by eliminating one or more undercuts. The method may further comprise the step of fabricating the dental retainer based on the digital model using a manufacturing device. The artificial intelligence model comprises a machine learning model, a deep learning model, or a combination thereof. The unique dental structures comprise various dental structures, dental conditions, or a combination thereof. The manufacturing device may comprise a 3D printer. The method may further comprise the step of adjusting the digital model based on one or more corrections received from a user or a dental professional.

The present invention eliminates material occupying the oral cavity and is aesthetically pleasing over the prior art. It also increases the accessibility of teeth for hygiene and minimizes discomfort. Due to its reduced size, the present invention does not interfere with the patient's speech or tongue space. The present invention is efficient to manufacture, and the resulting oral device is relatively easy to install in a wearer's mouth.

Other devices, apparatus, systems, methods, features, and advantages of the invention will become apparent to one with skill in the art upon examination of the following figures and detailed description. It is intended that all such additional systems, methods, features, and advantages be included within this description, as well as the scope of the invention, and protected by the accompanying claims.

BRIEF DESCRIPTION OF THE DRAWINGS

For a complete understanding of the present invention and its advantages, reference is now made to the ensuing descriptions taken in connection with the accompanying drawings briefly described as follows.

DETAILED DESCRIPTION OF PREFERRED EMBODIMENTS

Figure 1:
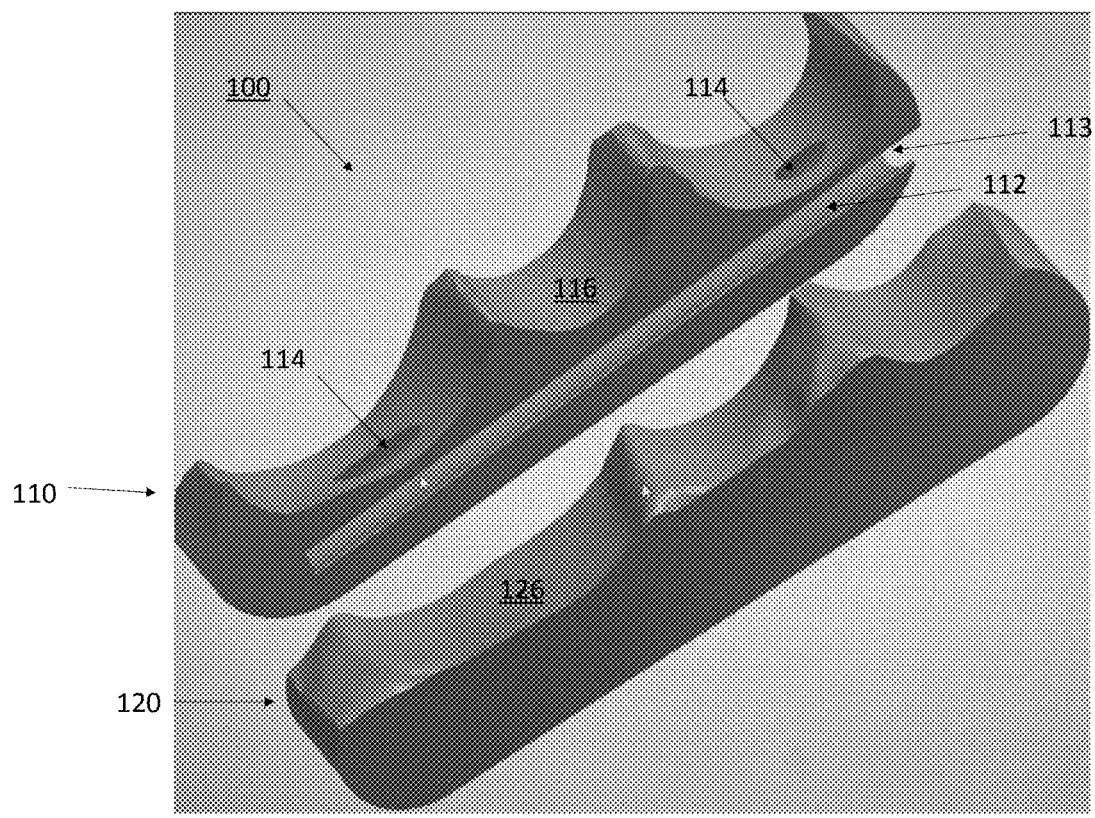
FIG. 1 illustrates a set of retainer bars for a left side of a mouth according to an embodiment of the invention.

Preferred embodiments of the present invention and their advantages may be understood by referring to FIGS. 1-36. Although the present invention is described in the context of inhibiting chewing and ingestion of solid food, the present invention may be used for any oral or orthodontic application where it is desirable to limit the movement of solid food with the mouth or restrict the movement of teeth.

In general, the present invention is an oral device attached to a wearer's jaw to interfere with the positioning of food on the teeth, thereby frustrating the wearer's ability to chew and ingest solid foods. The oral device comprises a flexible or foldable physical barrier on each side of the mouth that prevents the tongue from passing solid foods from the lingual portion of the oral cavity to the occlusal portion. These mastication barriers prevent food from moving between the occlusal surfaces of teeth, usually masticated by the premolars and molars, from moving back into the oral cavity, where it could be swallowed. Form-fitted retainers attached to or fitted over mandibular and maxillary teeth position the flexible food barriers on each lingual side of the oral cavity.

The embodiments of the present invention are advantageous in maintaining an all-liquid diet without impeding a wearer's ability to open and close the mouth for activities other than chewing, such as speaking, breathing, and yawning. There is no need to fully cover the teeth or utilize material on the buccal side of teeth, eliminating irritation to the user's lip and cheek lining and allowing better hygiene.

In one embodiment of the invention, the oral device comprises four retainer bars to position two flexible food barriers within the oral cavity. Two retainer bars are bonded to the mandible, and two more are bonded to the maxilla. Bonding is performed using dental cement or any other type of suitable adhesive, the identification and implementation of which are apparent to one of ordinary skill in the art, such as but not limited to dental composite resins. The term bonding cement, as used herein, includes not only dental cement but all types of suitable adhesives. Bonding is preferably semi-permanent, so the retainer bars may be removed later if desired. Each jaw set of retainers includes one retainer bar secured to the lingual surface of several teeth on the left side and one secured to the lingual surface of several teeth on the right side. In an embodiment of the invention, the teeth utilized for securing a respective retainer bar are limited to premolars and molars. The exact number of teeth used may vary depending on the number and size of teeth present and other oral parameters so long as the flexible barriers attached to it sufficiently inhibit mastication on the occlusal surfaces of the posterior teeth. In other embodiments of the invention, anterior teeth may also be included to secure a retainer bar.

As used herein, the term "bar" departs from its strict, plain, and ordinary meaning. The retainer bars of the present invention are not necessarily shaped like a long rod. They may be shaped in any manner to accommodate attachment to teeth and attachment to a corresponding flexible mastication barrier.

The term "retainer," as used herein, also includes a "tray" within its scope. In strict terminology, a retainer is a device worn to maintain a new position of teeth after an individual has undergone orthodontic treatment. A tray such as an Invisalign tray actively moves teeth and is not technically a retainer, though it may look similar. In the present invention, a retainer may retain or actively move teeth, and thus, the scope of such includes a tray.

Various components of the present invention may be manufactured from FDA-approved materials, the identification of which is apparent to one of ordinary skill in the art.

FIG. 1 illustrates a set of retainer bars 100 for a left side of a mouth according to an embodiment of the invention. The set of left retainer bars 100 comprises a mandibular retainer bar 110 and a maxillary retainer bar 120. The mandibular retainer bar 110 comprises a slot 112 and a slot entry 113. The slot 112 and the slot entry 113 receive a tab of a flexible mastication barrier, the attachment of which is described below. In an optional embodiment of the invention, there may be one or more openings 114 to minimize material or assist in securing the respective retainer. The mandibular retainer bar 110 includes teeth contact surface 116 contoured to match the lingual surface of a particular user's corresponding posterior teeth. Accordingly, the teeth contact surface 116 is prepared from a dental scan of the recipient's mouth, the identification and implementation of which are apparent to one of ordinary skill in the art. For example, any intraoral scanner may be used, including but not limited to 3D video, confocal imaging, structured light, laser, and LED pattern projection with appropriate digital processing, and software may be used to generate a digital representation of the teeth and oral cavity. The digital output of the dental scan is used to manufacture a custom-fitted retainer bar contoured to the recipient's teeth in this and other embodiments described herein. Accordingly, variations in the recipient's teeth' shape, size, and layout are accounted for to ensure maximum surface contact between a retainer bar and the corresponding teeth. The maxillary retainer bar 120 also includes a slot 122, a slot entry 123, and openings 124; however, these are hidden from view in this figure. They are shown in the following figures.

Figure 2:
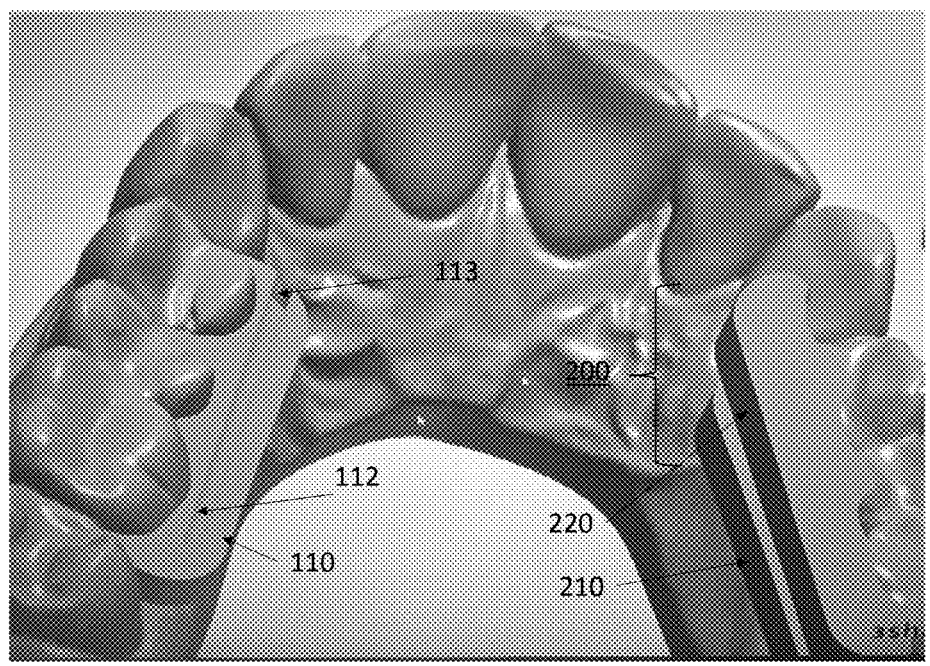
FIG. 2 illustrates a mandible with the mandibular retainer bar secured to mandibular posterior teeth according to an embodiment of the invention.

FIG. 2 illustrates a mandible with the mandibular retainer bar 110 secured to mandibular posterior teeth according to an embodiment of the invention. Here, the contour matching of the teeth contact surface 116 to the lingual surface of the mandibular posterior teeth is shown. Contour matching via a dental scan permits the lingual gaps between teeth and between teeth and a respective retainer bar to be occupied with retainer bar material. This gap-filling prevents the movement and ingestion of chewed food from the occlusal surfaces of the posterior teeth. Gap filling also better secures the respective retainer bars. Slot 112 is located on the top surface of the mandibular retainer bar 110. Moreover, the corners of the mandibular retainer bar 110 are rounded, as shown to minimize discomfort associated with the movement of a user's tongue. Any rough edges or transitions between surfaces may also be smoothed.

The right side of FIG. 2 depicts a set of retainer bars 200 for the right side of the mouth. The set of right retainer bars 200 comprises a mandibular retainer bar 210 and a maxillary retainer bar 220. The set of right retainer bars 200 includes the same elements described and shown concerning the set of left retainer bars 100, except that they are contoured and secured to the posterior teeth on the right side of the mouth. In FIG. 2, the mandibular retainer bar 210 is secured to the mandible. The mandibular retainer bar 210 includes a slot 212, a slot entry 213, an opening 214, and a teeth contact surface 216, shown in the following figures. To show its relative location when used with a corresponding flexible barrier, the maxillary retainer bar 220 is shown floating above the mandibular retainer bar, as the upper jaw is not included in this figure. The maxillary retainer bar 220 includes slot 222, slot entry 223, opening 224, and teeth contact surface 226, shown in the following figures.

Figure 3:
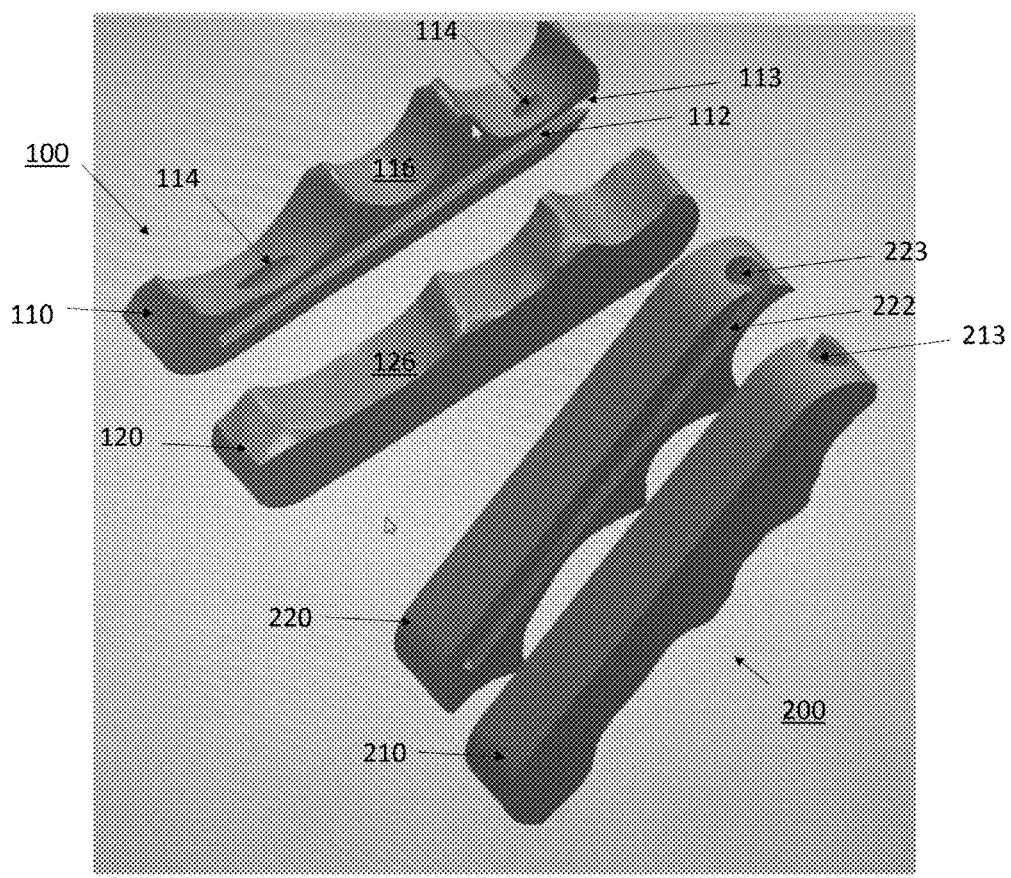
FIG. 3 illustrates a complete set of retainer bars according to an embodiment of the invention.

FIG. 3 illustrates a complete set of retainer bars 300 according to an embodiment of the invention. The complete set of retainer bars 300 comprises the set of retainer bars 100 for the left side of the mouth and the set of retainer bars 200 for the right side of the mouth. Here, slot 212 and slot entry 213 of the mandibular retainer bar 210 are better shown along with slot entry 223 for the maxillary retainer bar 220. Although slot 212 is shown as positioned on the lingual and palatal side, slot position may vary on any of the retainer bars so long as it does not interfere with the attachment of the respective mastication barrier.

Figure 4:
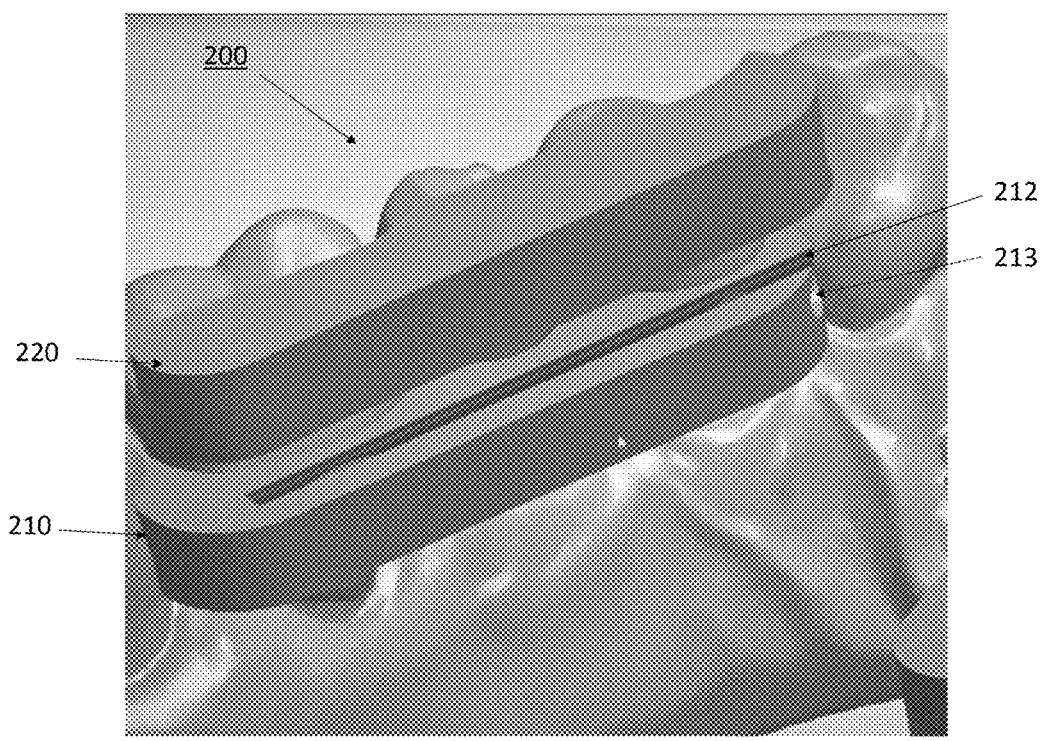
FIG. 4 illustrates a close-up view of the set of retainer bars for the left side of the mouth.

FIG. 4 illustrates a close-up view of the set of retainer bars 100 for the left side of the mouth. The mandibular retainer bar 210 is secured to the mandibular posterior teeth. To show its relative location when used with a corresponding flexible barrier, the maxillary retainer bar 220 is shown floating above the mandibular retainer bar 210, as the upper jaw is not included in this figure.

Figure 5:
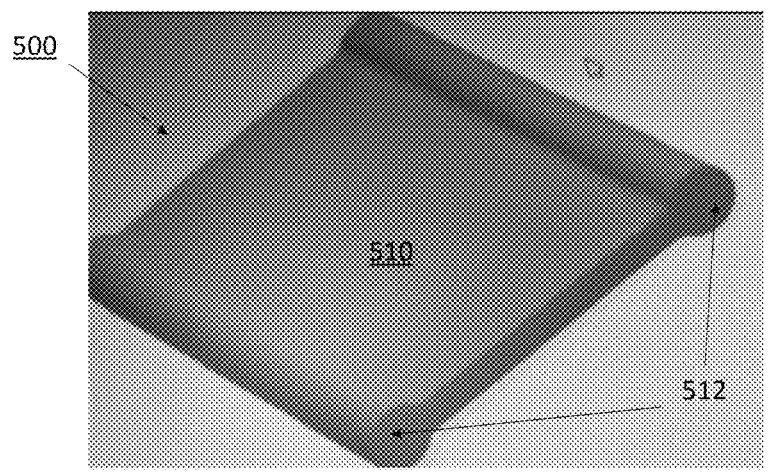
FIG. 5 illustrates a mastication barrier according to an embodiment of the invention.

FIG. 5 illustrates a mastication barrier 500 according to an embodiment of the invention. A mastication barrier 500 will be used on each side of the mouth, i.e., in both the set of retainer bars 100 for the left side and the set of retainer bars 200 for the right side. The dimensions of the mastication barrier 500 may vary between the two sets to accommodate any mouth asymmetry. The mastication barrier 500 comprises a body 510 disposed between a tab 512 at one edge and another at an opposite edge. Each tab 512 slides into a respective slot 112, 122, 212, or 222 of a set of retainer bars 100 or 200 via corresponding openings 113, 123, 213, or 223. In other words, slots 112, 122, 212, and 222 and tabs 512 correspond to female and male connectors. This slot and tab configuration is easy for a dental professional to install and is comfortable for the wearer.

The mastication barrier 500 is preferably a deformable elastic material to form a pressure-fit connection with the retainer bars. In an embodiment of the invention, the body 510 and tabs 512 are integrated as a single material. Exemplary materials include but are not limited to neoprene, silicone, and synthetic or natural rubber. However, more rigid materials such as polymers, ceramics, metals, and metal alloys may be used, including materials often used in dental implants like zirconia. These materials may also be used in the other embodiments described below. More preferably, the body 510 experiences minimal or no folding when the user's mouth is closed, which allows the user to open their mouth without any undue effort. In other embodiments, the body and tabs 512 are two materials joined together. For example, tabs 512 may be formed from a sufficiently rigid or non-deforming material, facilitating their seamless insertion into the slots of the retainer bars.

Figure 6:
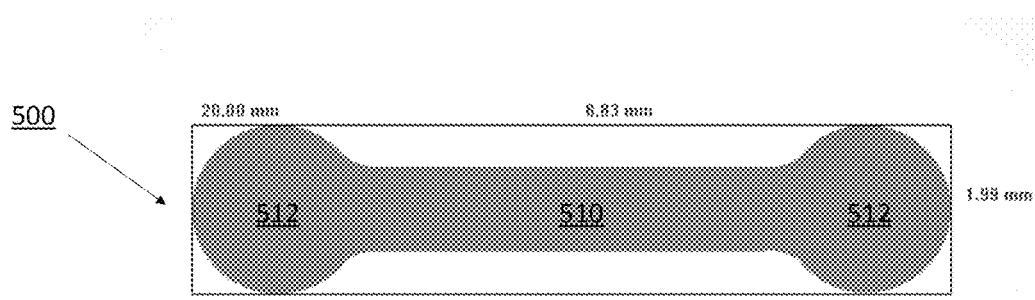
FIG. 6 is an end view of the flexible barrier and its dimensions according to an exemplary embodiment of the invention.
Figure 7:
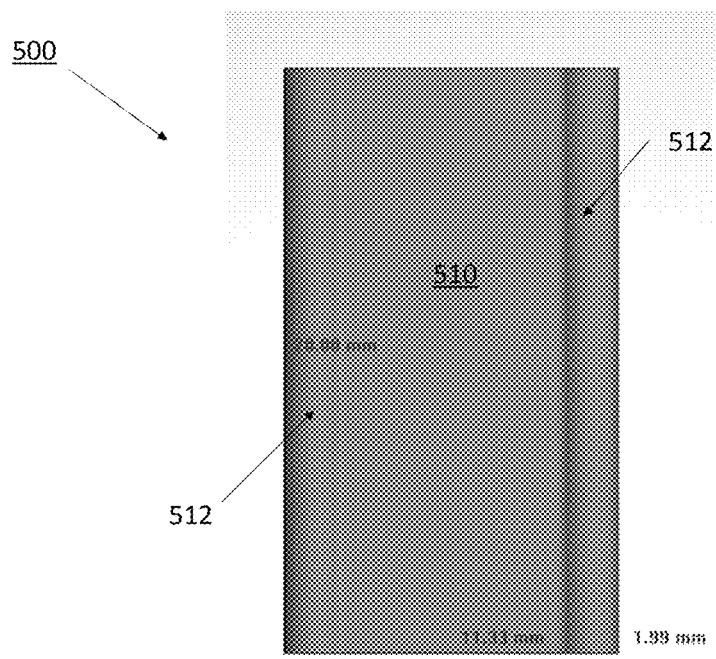
FIG. 7 is a top view of the flexible barrier and its dimensions according to an exemplary embodiment of the invention.

FIGS. 6 and 7 illustrate the dimensions of the flexible barrier 500 according to an exemplary embodiment of the invention. For example, the tabs 512 are cylindrical with a diameter of 1.95-2.00 mm. The slots will have a corresponding but slightly smaller diameter (e.g., a connector diameter of 1.998 mm for a cylindrical cavity diameter of 2.000 mm). Different geometries may be implemented for retainer bar attachment in other embodiments, such as square, rectangular, hexagon, or triangular shapes. Such geometries may be slid into place in matching counterpart slots or have an alternative locking geometry that a dental professional can secure during placement.

Figure 8:
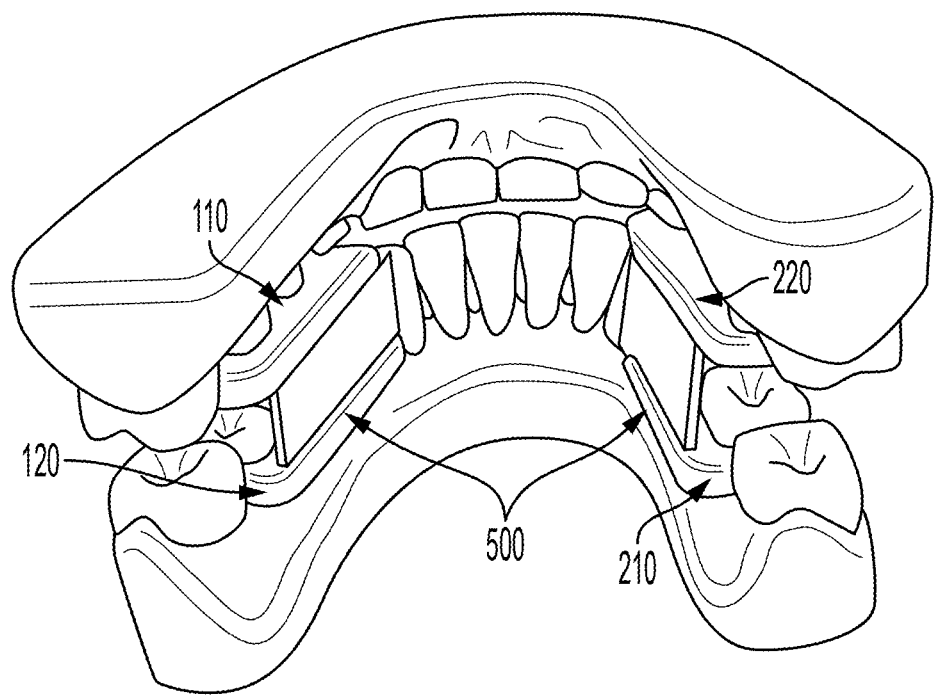
FIG. 8 illustrates a rear view of a complete oral device according to an embodiment of the invention in a replica of a user's mandible and maxilla.
Figure 9:
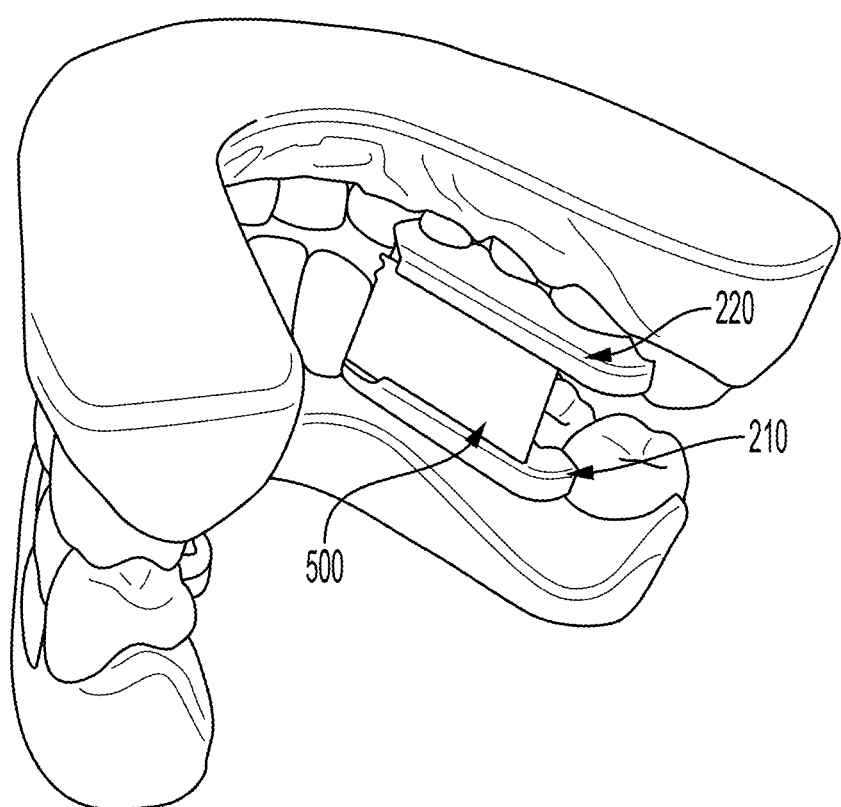
FIG. 9 illustrates a side-rear view of the complete oral device shown in FIG. 8.

FIGS. 8 and 9 illustrate a complete oral device 800 according to an embodiment of the invention in a mockup jaw. The oral device 800 comprises a set of retainer bars 100 for the left side of the mouth and a set of retainer bars 200 for the right side of the mouth. The set of retainer bars 100 are coupled to one another through the flexible mastication barrier 500. Likewise, the set of retainer bars 200 are coupled to one another through another flexible mastication barrier 500. To enhance contrast, the barriers 500 are annotated in black. In practice, the retaining bars are designed to mimic the color of teeth, and transparent flexible barriers are used. The oral device 800 forms a physical barrier on each side of the mouth sufficient to prevent solid foods from reaching the occlusal surfaces of the posterior teeth, thereby compelling users to follow a liquid diet as solid food cannot be chewed and ingested.

The length of each retaining bar can vary from a single tooth, approximately 7 mm, to four teeth, approximately 30 mm, depending on the dimensions of the wearer's posterior teeth. In one exemplary embodiment, the retainer bars have external dimensions of 3-5 mm in height by 3.5-5 mm in width (extending mesially to distally in the lingual and palatal portions of the surface of the teeth to which the retainers/bars are attached), and generally 25-26 mm length for most users. The exact dimensions may be calibrated based on a scan of a user's oral anatomy such that there is a minimum 4.360 mm vertical clearance between the palatal and lingual retainers on each side and approximately 23.52 mm horizontal clearance between the left and right retainers inside the oral cavity. This helps ensure adequate space for the wearer's tongue to rest and move for purposes other than chewing without discomfort.

Figure 10:
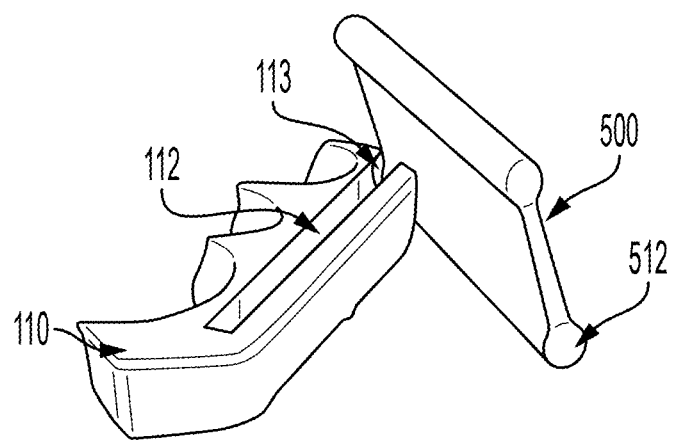
FIG. 10 illustrates a mastication barrier 500 and a retainer bar 110 in a disassembled state.
Figure 11:
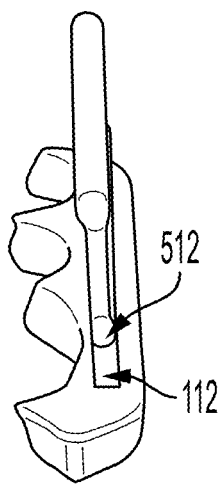
FIG. 11 illustrates a tab of the mastication barrier partially inserted into the slot of the retainer bar of FIG. 10.
Figure 12:
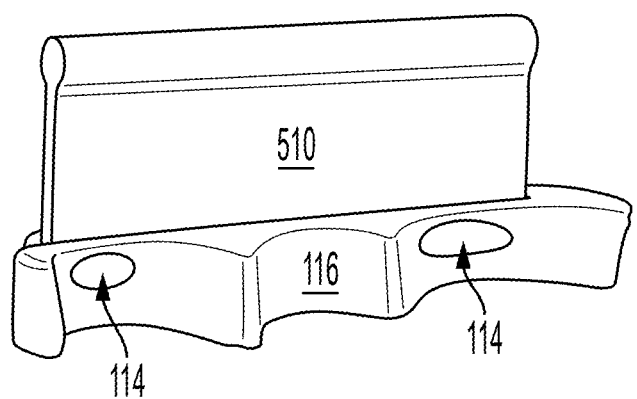
FIG. 12 illustrates the mastication barrier fully inserted into the retainer bar of FIG. 10.

FIGS. 10-12 illustrate a mastication barrier 500 joining with a retainer bar 110. The mastication barrier 500 is a rigid mockup and would otherwise have a flexible body 510 in practice. Referring to FIG. 10, the mastication barrier 500 and the retainer bar 110 are disassembled. Referring to FIG. 11, tab 512 of the mastication barrier 500 is inserted into slot 112 of the retainer bar 110 starting at opening 113. Referring to FIG. 12, the mastication barrier 500 and the retainer bar 110 are fully assembled. Once in position, a dental professional may semi-permanently secure the tab 512 to retainer bar 110 by placing cement at holes 114.

Figure 13:
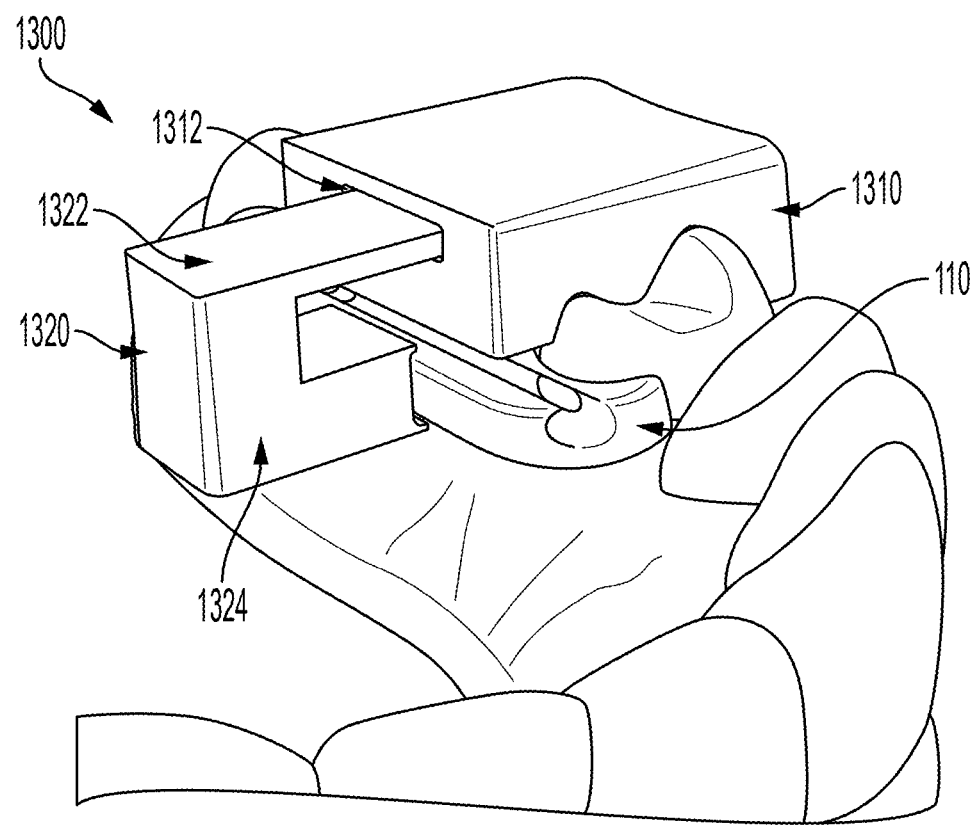
FIG. 13 illustrates an optional jig according to an embodiment of the invention.

FIG. 13 illustrates an optional jig 1300 according to an embodiment of the invention. The jig 1300 facilitates the accurate placement and attachment of the retaining bars to the teeth. The jig 1300 comprises two interlocking and removable pieces: a jig check 1310 and a retainer holder 1320. The jig check 1310 fits onto the occlusal surface of the teeth and features a rectangular slot 1312. The retainer holder 1320 is a U-shaped piece with two arms, 1322 and 1324. The lower arm 1324 of the retainer holder 1320 secures a retainer bar, in this case, retainer bar 110 to the user's teeth, while the upper arm 1322 fits through the rectangular slot 1312 in the jig check 1310. The bottom surface (or top surface if used on the maxilla) of the jig check 1310 is contoured to match the occlusal surface, a portion of the lingual surface, and a portion of the buccal surface of a portion (as shown) or all (not shown) of the posterior teeth for which the retainer bar 110 is to be attached. The contoured surface is prepared from a dental scan of the recipient's teeth. The dimensions of the jig check 1310, upper arm 1322, and lower arm 1324 are determined based on the dental scan and the desired placement of the retainer bar 110.

Figure 14:
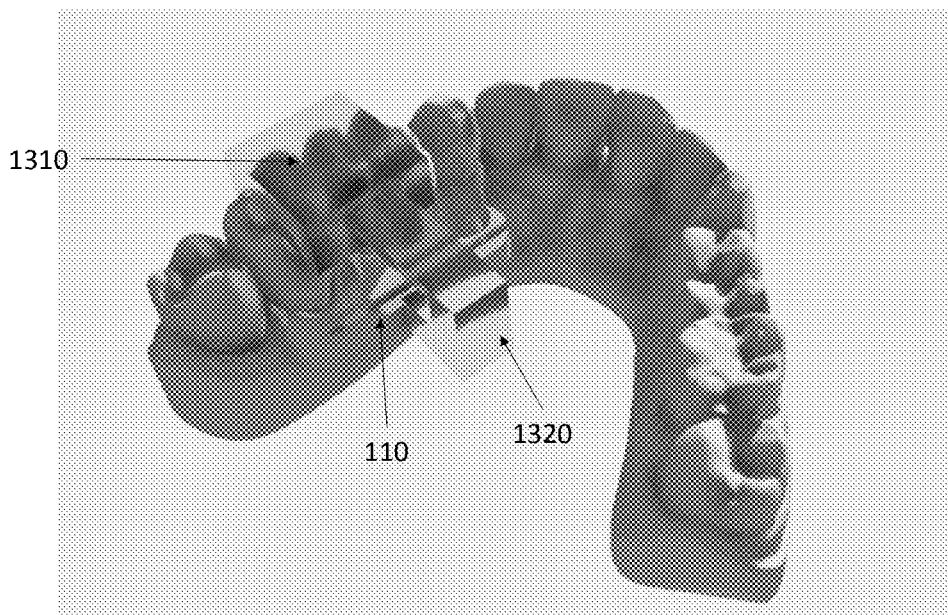
FIG. 14 depicts the optional jig of FIG. 13 as transparent to show the teeth and retainer bar underneath.

When fitted over the user's teeth, the jig check 1310 restricts movement of the posterior teeth underneath it and ensures proper vertical and lateral positioning of the respective retainer bar 110. During placement, the jig check 1310 temporarily covers portions of both the lingual and buccal sides of the wearer's teeth, effectively locking the retainer bar 110 via the retainer holder 1320 in place for bonding by the dental professional. The jig 1300 is removed after the bonding cement is adequately cured. To show the positioning of the jig 1300 over the posterior teeth, FIG. 14 depicts the optional jig 1300 as a transparent replica. A custom jig 1300 is prepared for each respective retainer bar 110, 120, 210, and 220. In an embodiment of the invention, the jig check and retainer holder are integrated as a single component.

Figure 15:
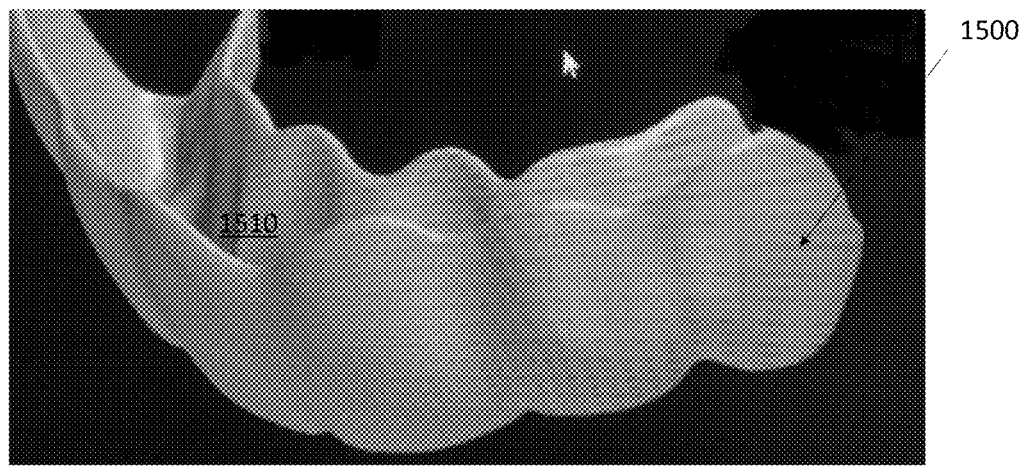
FIG. 15 illustrates an aligner for anterior teeth according to an embodiment of the invention.

FIG. 15 illustrates an aligner 1500 according to an embodiment of the invention. Aligner 1500 includes a teeth surface 1510 contoured to the anterior teeth or anterior teeth and posterior teeth that are not bonded to the retainer bars utilized on the mandible or maxilla. The aligner 1500 is prepared from a dental scan of the teeth it covers and, when used, restrains or forces slight movement of the covered teeth in a desired position. As shown, the teeth surface 1510 is contoured to the respective teeth' lingual, occlusal, and buccal surfaces. Aligner 1500 fills the space of teeth between the retainer bars bonded to the mandible or maxilla. The aligner 1500 is removable and thus can be used as a temporary retainer during, for example, sleeping. Alternatively, the aligner can be worn at all times except during drinking, e.g., consuming a liquid diet. The aligner 1500 may be manufactured from a clear, rigid plastic.

Figure 16:
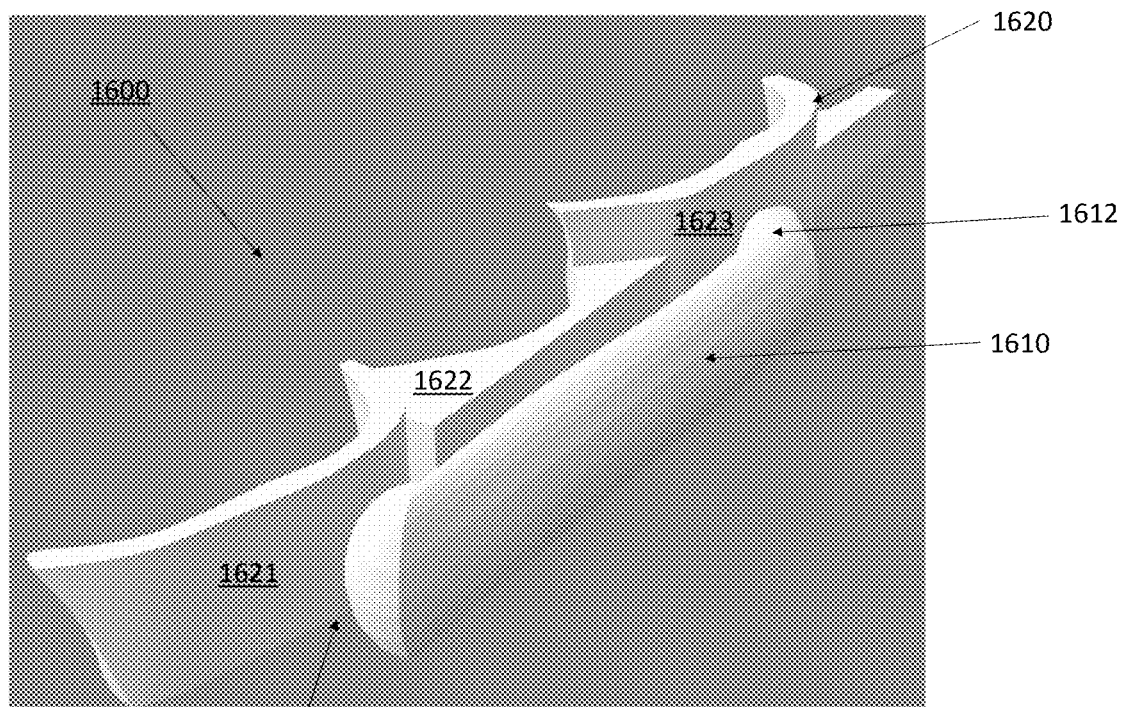
FIG. 16 illustrates a retainer bar according to another embodiment of the invention.

FIG. 16 illustrates a retainer bar 1600 according to another embodiment of the invention. The retainer bar 1600 comprises a handle arm 1610 and a teeth band 1620. The handle arm 1610 is integrated into the teeth band 1620 through elbow 1612. The handle arm 1610 extends from the elbow 1612 in a manner that is generally parallel to the teeth band 1620. However, an opening 1614 is present between the handle arm 1610 and the teeth band 1620 on the handle arm 1610 end opposite the elbow 1612. The teeth band 1620 includes sections 1611, 1612, and 1613 contoured to a portion of the lingual surface of the respective teeth, in this case, three posterior teeth; however, the actual number may vary in practice. The teeth sections 1611, 1612, and 1613 form a teeth contact surface developed from a dental scan of the respective teeth. Optionally, one or more of the tooth sections 1611 may serve as an arch between tooth sections. For example, teeth section 1612 may serve as an arch between tooth section 1611 and tooth section 1613. The arch does not come in contact with the lingual surface of a tooth. For simplification, only one retainer bar 1600 is shown; however, four retainer bars will be used in the complete oral device: one for the mandibular posterior teeth on the left side of the mouth, one for the maxillary posterior teeth on the left side of the mouth, one for the mandibular posterior teeth on the right side of the mouth, and one for the maxillary posterior teeth on the right side of the mouth.

Figure 17:
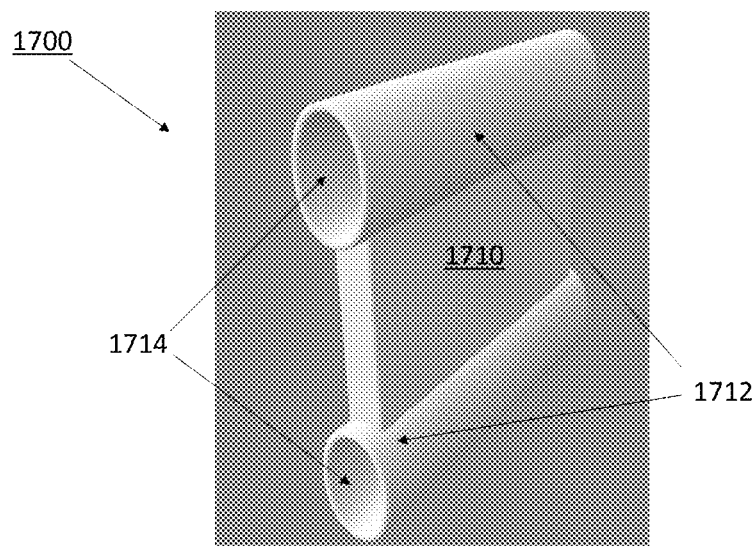
FIG. 17 illustrates a mastication barrier for use with the retainer bar of FIG. 16.

FIG. 17 illustrates a mastication barrier 1700 for use with two retainer bars 1600. Like mastication barrier 500, the mastication barrier 1700 comprises a body 1710 and tabs 1720. However, in this embodiment, the tabs 1720 are hollow cylinders configured to receive a handle arm 1610 snugly to secure the mastication barrier 1700 to two retainer bars 1600 on the left or right side of the recipient's mouth. The distal end of the handle arm 1610 may include a protrusion or notch at opening 1614 to prevent a tab 1720 from sliding off the handle arm 1610.

Figure 18:
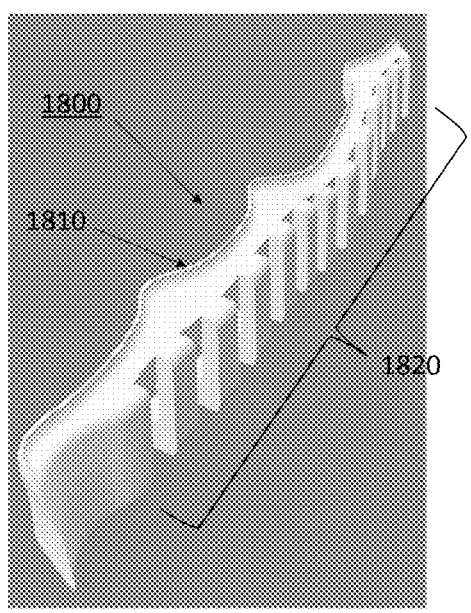
FIG. 18 illustrates a top view of a retainer bar according to another embodiment of the invention.
Figure 19:
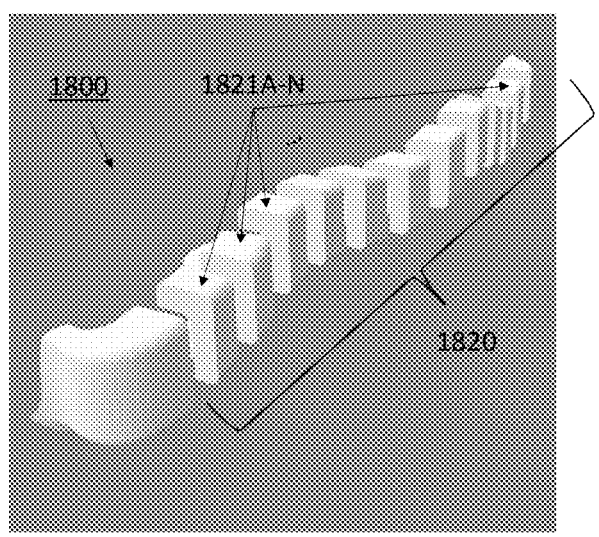
FIG. 19 illustrates a bottom view of the retainer bar of FIG. 18.

FIGS. 18 and 19 illustrate a retainer bar 1800 according to another embodiment of the invention. FIG. 18 illustrates a top view of the retainer bar 1800, and FIG. 19 illustrates a bottom view. Here, the retainer bar 1800 comprises teeth contact surface 1810 on one side and an array of hooks 1820 on the opposite side. Here, the retainer bar 1800 is formed as an integrated single piece of material. The array of hooks 1820 comprises a number (N) of individual hooks 1821A-N running along the length of the retainer bar 1800 to provide a fastening means for securing an edge of a mastication barrier, which is further described below. Hooks 1821A-N may be L- or J-shaped. The number N of individual hooks 1821N may be any number suitable for adequately securing a respective mastication barrier. The teeth contact surface 1810 is contoured using a dental scan to match the lingual surface of the respective posterior teeth for which it is secured. For simplification, only one retainer bar 1800 is shown, however four retainer bars will be used in the complete oral device as described above.

Figure 20:
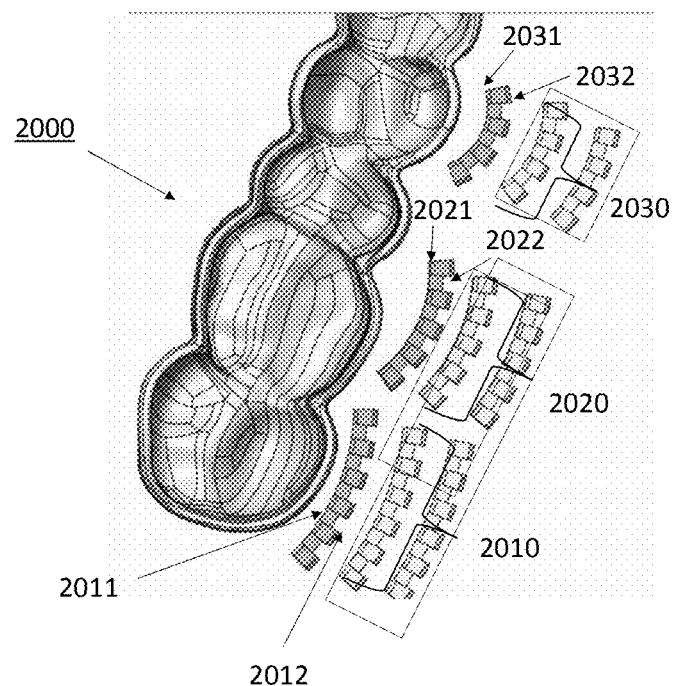
FIG. 20 illustrates a segmented retainer bar according to another embodiment of the invention.

FIG. 20 illustrates a segmented retainer bar 2000 according to another embodiment of the invention. The segmented retainer bar 2000 is similar to retainer bar 1800 in that it includes hooks; however, it has been segmented into sections 2010, 2020, and 2030. Each section 2010, 2020, or 2030 includes a tooth contact surface 2011, 2021, or 2031 and an array of hooks 2012, 2022, or 2032. Each array of hooks comprises a number of individual hooks spaced along the section, sufficient to secure a portion of the edge of a mastication barrier. The advantage of the segmented retainer bar 2000 is that each section 2010, 2020, and 2030 may be cut from a length of continuous and flexible retainer bar material. The length of each section corresponds to a portion of the respective tooth's lingual circumference. Each flexible section is then bonded to the respective tooth, eliminating the need for a dental scan.

Figure 21:
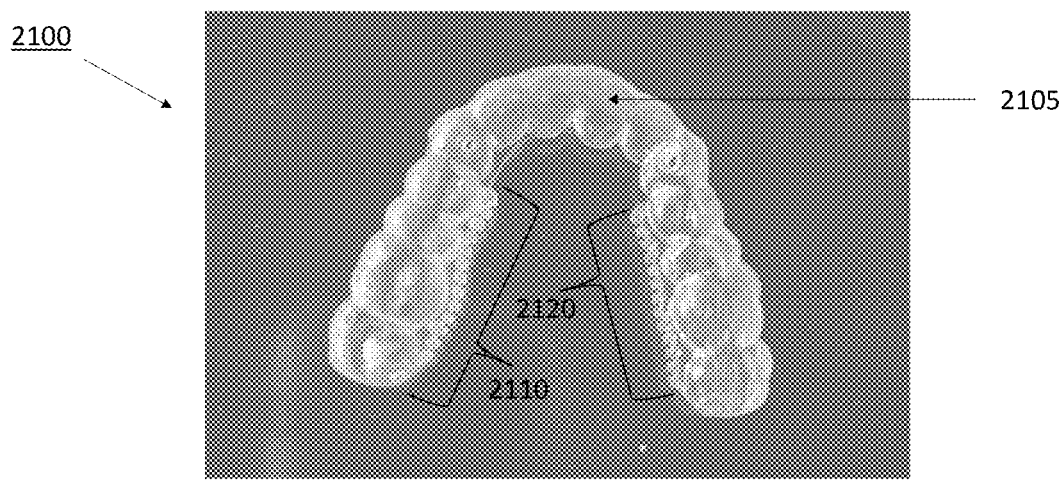
FIG. 21 illustrates a retainer system according to an embodiment of the invention.

FIG. 21 illustrates a retainer system 2100 according to another embodiment of the invention. The retainer system 2100 comprises a retainer 2105 with integrated retainer bars 2110 and 2120 on the respective lingual surface of each side of the mouth. Only one retainer 2105 is shown for the mandible. A complementary retainer (not shown) would be used for the maxilla.

Figure 22:
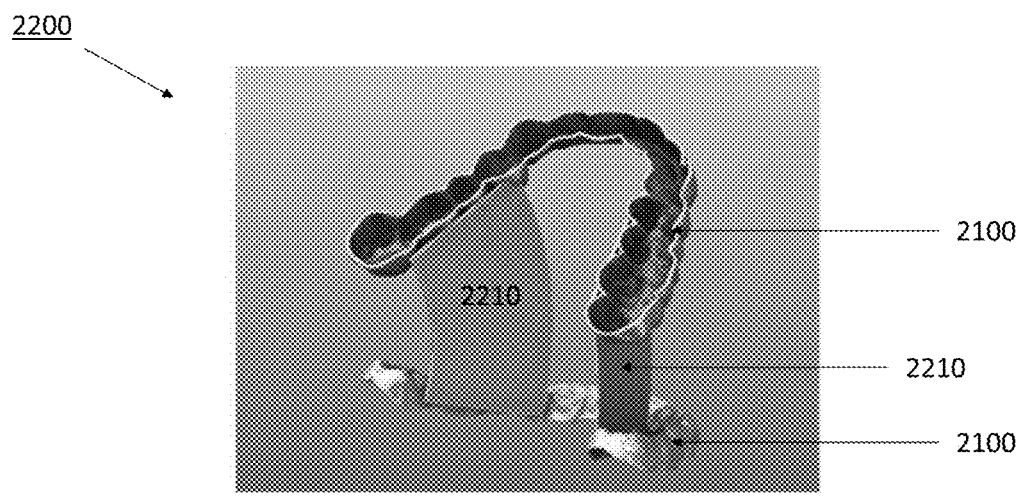
FIG. 22 illustrates an oral device according to an embodiment of the invention.

FIG. 22 illustrates an oral device 2200 according to an embodiment of the invention. Here, the oral device 220 comprises a pair of retainer systems 2100 connected through mastication barriers 2210. The integrated retainer bars 2110 and 2120 are obstructed from view. The mastication barriers 2210 are flexible and stretch, allowing the user's mouth to open to the maximum biological extent. In one embodiment, minimal, if any, folding of the mastication barriers 2210 occurs when the mouth is closed. The degree of elasticity of each flexible mastication barrier 2210 may vary to provide different degrees of resistance. In another embodiment, the mastication barriers 2210 may fold toward the tongue or cheek, or folding may be limited between the teeth.

Figure 23:
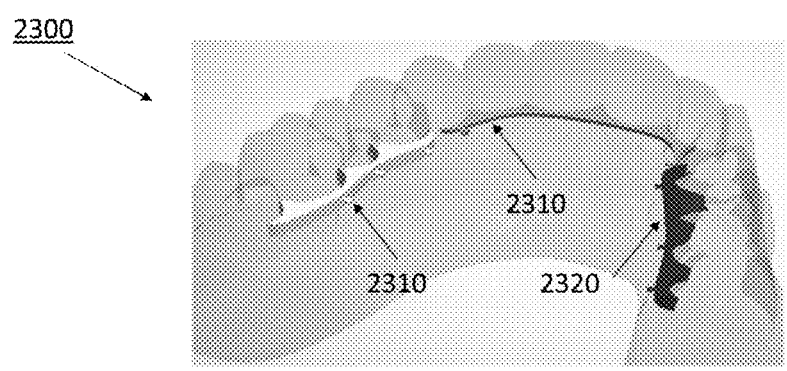
FIG. 23 illustrates a retainer system according to an embodiment of the invention.

FIG. 23 illustrates a retainer system 2300 according to an embodiment of the invention. Here, the retainer system 2300 comprises a retainer 2310 attached to the posterior teeth on the left side, a retainer bar 2320 attached to the posterior teeth on the right side, and a retainer bar 2330 attached to the anterior teeth of the mandible. A complementary retainer system (not shown) would be used for the maxilla. The retainer bars 2310 and 2320 are secured to a set of mastication barriers as described above. The retainer bar 2330 minimizes, if not wholly prevents, super-eruption of the teeth not secured to retainer bars 2310 and 2320. In other words, the teeth not utilized for securing the mastication barriers are held in place by a separate retainer in this embodiment. In other embodiments, the retainer bar 2330 is used with a portion or all of the teeth not used for the retainer bars 2310 and 2320 and may include one or more posterior teeth or less than all of the anterior teeth.

The retainer bar 2330 may be used as a standalone device. In one embodiment, it can be made of a thermoplastic material such as polyurethane, polyethylene terephthalate glycol (PETG), or polyvinyl chloride (PVC), which are known in commercial use for their durability, transparency, and biocompatibility. The anterior retainers are custom-made in one embodiment to fit the user's teeth. They are designed to be inconspicuous while providing the necessary support to prevent teeth from shifting back to their original positions.

Figure 24:
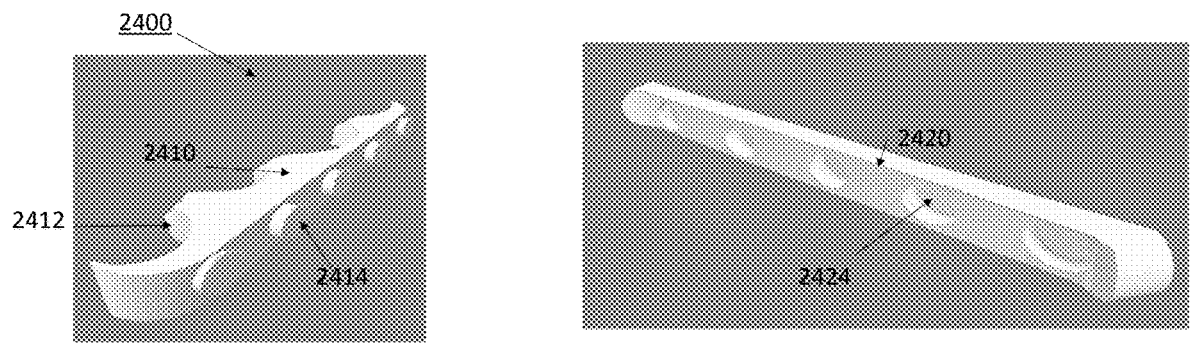
FIG. 24 illustrates a two-component retainer bar connection system according to an embodiment of the invention.

FIG. 24 illustrates a two-component retainer bar connection system 2400 according to an embodiment of the invention. Here, the retainer bar system 2400 comprises a first component 2410 with a teeth contact surface 2412 contoured to the user's teeth as described above and a second component 2420 that interlocks with the first component 2410. On its opposite side, the first component 2410 has a set of male connectors 2414. The second component 2420 includes a set of corresponding female connectors 2424. When coupled, the male connectors 2414 and female connectors 2424 provide an interference fit to secure the edge of a mastication barrier between the first component 2410 and the second component 2420. Such a connection system may also connect the opposite edge of the mastication barrier.

Figure 25:
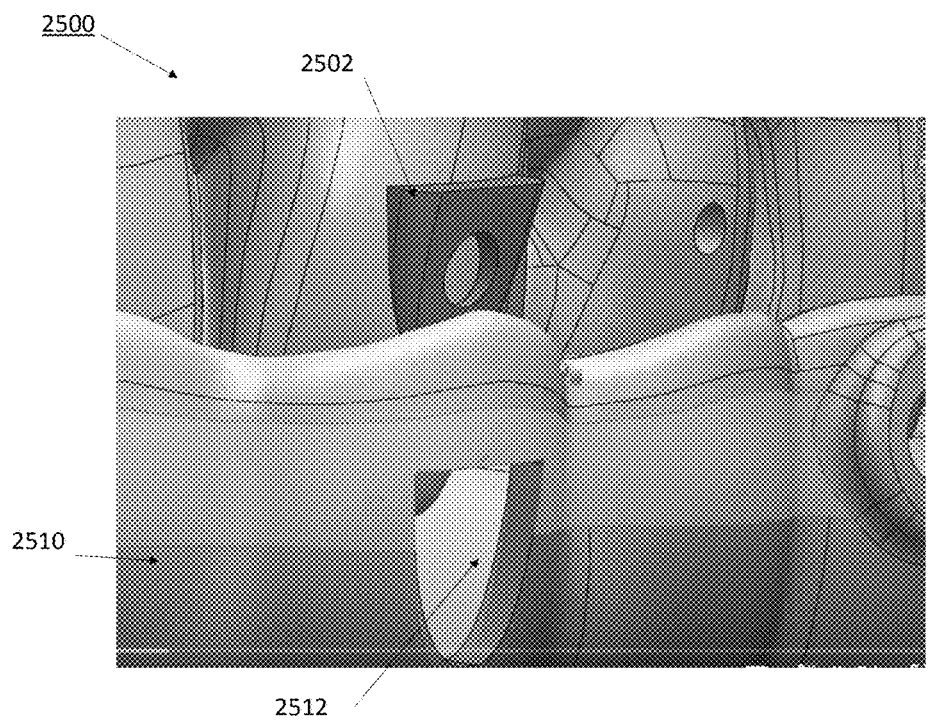
FIG. 25 illustrates a retainer attachment system according to an embodiment of the invention.

FIG. 25 illustrates a retainer attachment system 2500 for attaching a retainer or retainer bar as described above according to an embodiment of the invention. The attachment system 2500 comprises one or more projections 2502 affixed to the user's teeth. A retainer 2510 (e.g., a full retainer as in FIG. 21 or, alternatively, one of the retainer bars described in the systems above) comprises one or more correspondingly shaped notches 2512. The projection 2502 and notch 2510 are configured to provide an interference fit to keep the retainer 2510 in place when pressed against the projection 2502. Although the projection 2502 and corresponding notch 2512 are depicted as triangular, other geometric shapes may be used. In this embodiment, the base side of the triangular-shaped projection 2502 and notch 2512 is disposed near the occlusal surface of the teeth.

Figure 26:
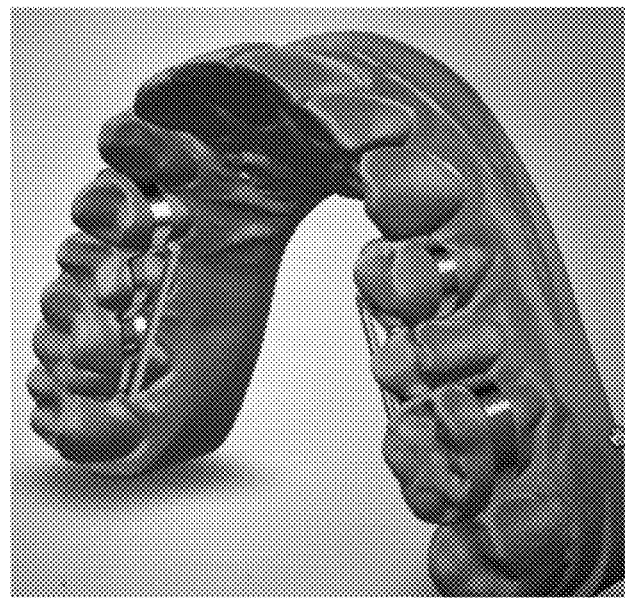
FIG. 26 illustrates a retainer system according to an embodiment of the invention.

FIG. 26 illustrates a retainer system 2600 according to an embodiment of the invention. Here, the retainer bar system 2600 comprises a retainer bar 2610 constructed of bands 2612 fitted around posterior teeth. Affixed to one or more bands 2612 is a bar 2614 to attach a mastication barrier. The bands 2612 may be manufactured from a solid material such as but not limited to metal or flexible material that can be friction-fitted over teeth. The bar 2614 is preferably rigid to provide a secure mount for a mastication barrier. Two or four retainer systems 2600 would be used to form a complete oral device.

To improve fabrication and accuracy of the fit of retainers like retainer 2105 over the mandible or maxilla, an artificial intelligence (AI) platform based on a deep convolutional neural network (CNN or DCNN) architecture is implemented to predict and remove undercuts. An undercut is the cross-sectional portion of the retainer that prevents it from being inserted or fitted over the corresponding teeth. For example, many teeth are wider at their occlusal surface than at the gum. Before this invention, fabrication required a lengthy process of scanning teeth, sending the scans off-site, and then hand-creating custom-fit retainers. This process is also labor intensive and requires skilled dental lab technicians trained in design software such as Solidworks or 3Shape and 3D printing. To streamline this process most accurately, the present invention rapidly corrects and fills in undercuts around the teeth and gums and between the teeth in the interproximal areas and black triangles to avoid locking in the retainers/appliances. It also corrects any distortions in the scans and thus designs the retainers and attachments and outputs data files to facilitate 3D-printed with precision to ensure an optimal fit and user comfort. AI printing of retainer pieces and barriers has yet to be implemented in commercial practice.

Utilizing an AI platform for design can ensure improved fit in retainers over traditional laboratory techniques, which facilitates attachment of retainer pieces to a user's teeth with less effort and finesse required on the part of the dental professional. Further, using AI for design reduces fabrication costs and savings, which can be passed to consumers to make the invention, facilitating a weight loss program available to all economic classes.

Figure 27:
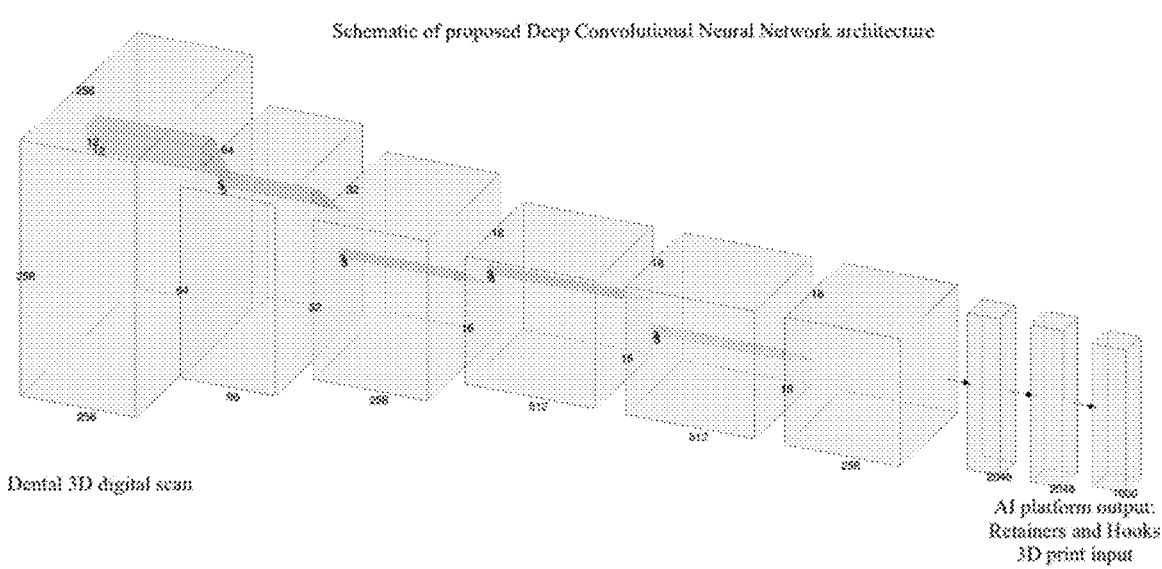
FIG. 27 illustrates a schematic of an artificial intelligence platform according to an embodiment of the invention.
Figure 28:
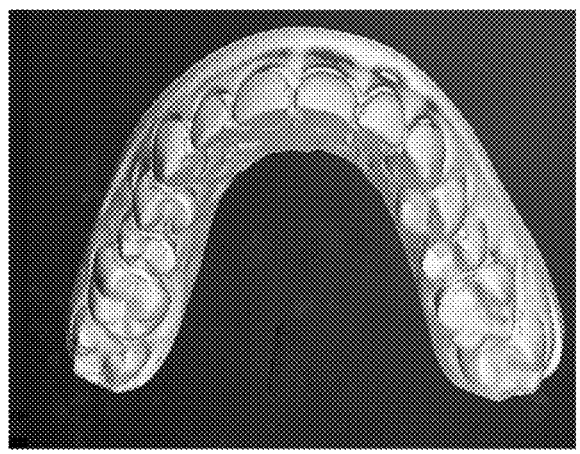
FIG. 28 illustrates an initial pass at filling in undercuts.

Though sophisticated software is used, every dimension and feature must be precisely defined using complex, domain-specific software tools to produce a usable design ready for manufacturing. FIG. 27 depicts a schematic of a DCNN architecture according to an embodiment of the invention. AI algorithms are created and trained to design the retainer bars and barriers to implement this structure. The designed retainers and barriers are produced in STL format and then sent to a 3D printer and printed. This forms a custom-fit retainer for each user.

In an embodiment of the invention, the AI algorithms are trained using 500-1,000 scans of the target dentition, covering both the upper and lower arches prepared with the undercuts present in natural dentition being strategically filled in. Teeth are anatomically unique, each serving specific functions in chewing, speaking, and aesthetics, which makes it challenging to create a generic retainer that fits all. Currently, each retainer is individually designed by a lab technician, manually or using computer programs, which is a labor-intensive process. This AI platform aims to streamline the retainer design process using a large dataset to train the platform through machine learning. This will simplify the design process by addressing issues such as undercuts-areas where teeth widen on the chewing surface and narrow towards the gumline, potentially causing plastics to get stuck. Lab technicians currently spend considerable time smoothing these undercuts to facilitate easier placement and removal of retainers. The platform aims to automate and optimize the retainer design process by utilizing machine learning, improving efficiency and precision in creating custom-fit retainers.

Figure 29:
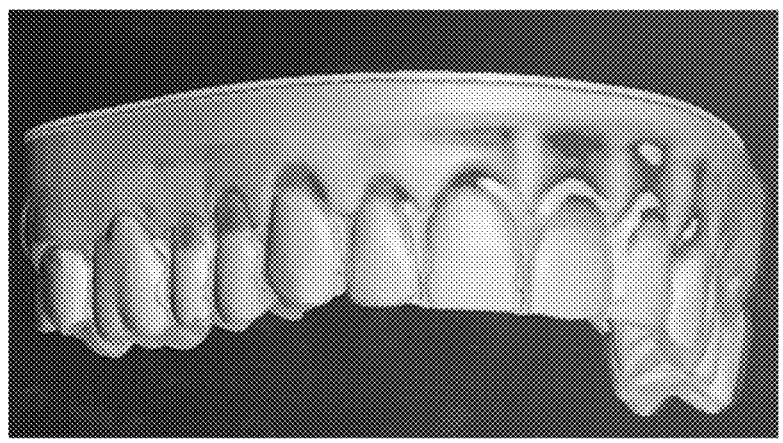
FIG. 29 illustrates a second pass at filling in undercuts.
Figure 30:
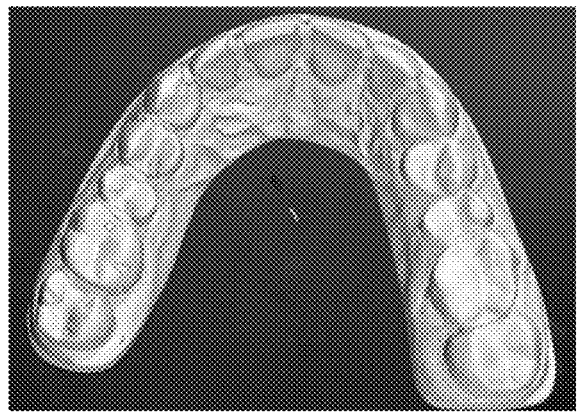
FIG. 30 illustrates a final pass at filling in undercuts.
Figure 31:
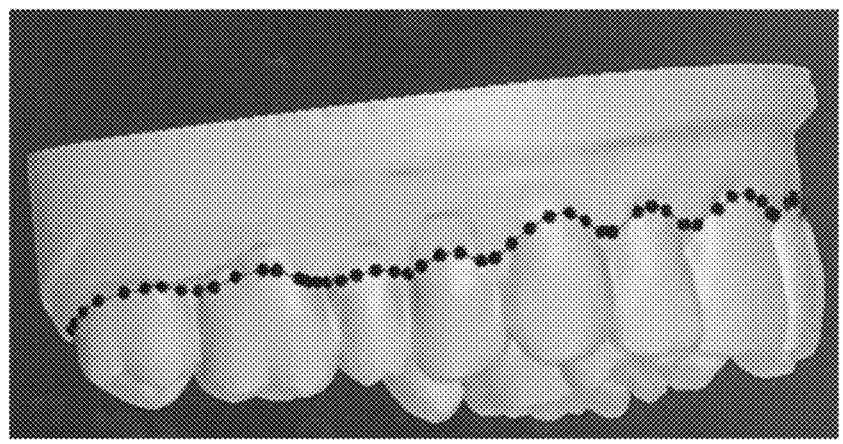
FIG. 31 illustrates a side view of delineating a full retainer's gum-adjacent outline.
Figure 32:
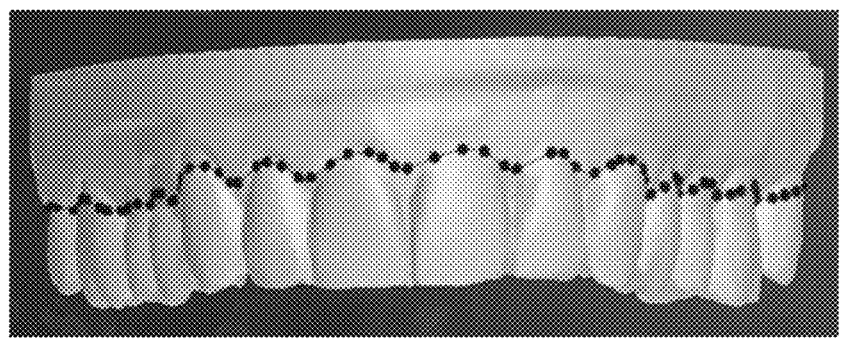
FIG. 32 illustrates a front-to-back view of a full retainer's gum-adjacent outline delineation.
Figure 33:
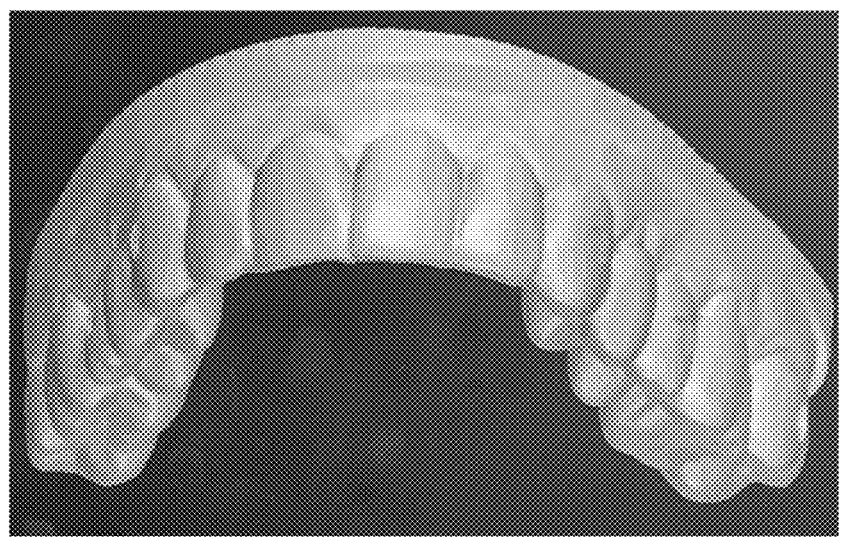
FIG. 33 illustrates a completed retainer design.
Figure 34:
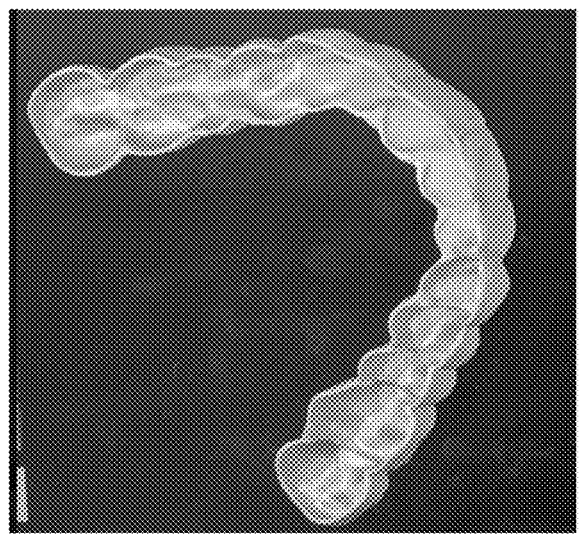
FIG. 34 illustrates a rendering of an exemplary retainer design in STL format ready for a 3D printer.
Figure 35:
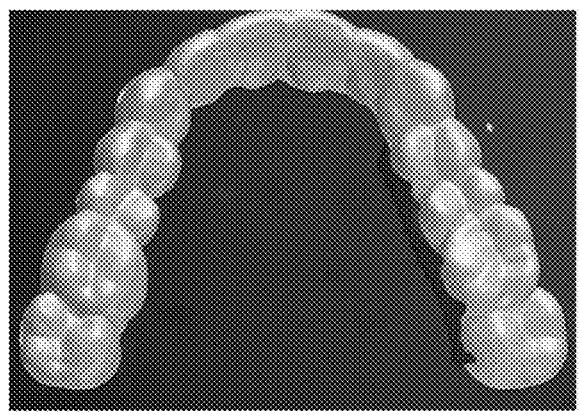
FIG. 35 illustrates a top-down view of hooks added to an exemplary retainer design.
Figure 36:
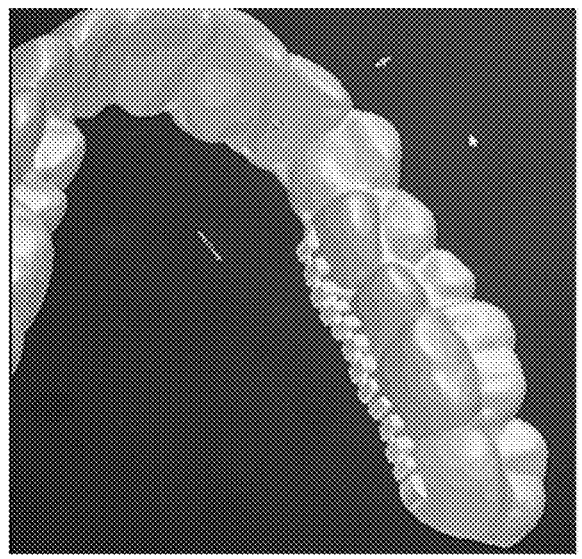
FIG. 36 illustrates a side view of hooks added to an exemplary retainer design.

As the algorithms used in AI learning improve, the automated identification of the undercuts becomes faster and more accurate. After the 500-1,000 training scans are completed, the AI can efficiently eliminate undercuts and establish appropriate borders for retainer fabrication. Using AI to complete this process allows the time of processing to be reduced from a matter of hours to a matter of seconds. The progression of this learning can be observed in FIG. 28, which demonstrates a first pass by the AI at filling in the undercuts; FIG. 29, a second pass; and FIG. 30, a final pass. Once the processing of FIGS. 28-30 was completed, and the delineation of the retainer's optimal gum barrier can be seen in FIGS. 31-32. FIG. 33 depicts the final retainer design. Once the final retainer design has been identified, an STL file containing that structure is generated and sent to a 3D printer. FIG. 34 depicts a retainer design ready to be sent to a 3D printer in STL format. FIGS. 35 and 36 illustrate the process of adding hooks for barrier connection to the designed printer. The use of the AI platform simplifies the process of adding or subtracting elements and ensures perfect matches between connection points on the retainer and barrier portions of the invention. Once the STL file has been generated, an appropriate slicer program is selected, appropriate medical-grade materials are chosen, and the STL is forwarded to the 3D printing machine. At the 3D printer, the slicer converts the STL into printable G-Code. The 3D printer then generates a custom fit retainer for the user.

While the invention has been described in connection with a number of embodiments and implementations, the invention is not so limited but covers various apparent modifications and equivalent arrangements, which fall within the purview of the appended claims. Although features of the invention are expressed in certain combinations among the claims, it is contemplated that these features can be arranged in any variety and order. The invention has been described herein using specific embodiments for illustrative purposes only. It will be readily apparent to one of ordinary skill in the art, however, that the principles of the invention can be embodied in other ways. Therefore, the invention should not be limited in scope to the specific embodiments disclosed herein; it should be fully commensurate with the following claims.

I claim:

1. A method of creating a retainer comprising the steps of:
receiving a dental scan representing a dental structure;
processing the dental scan using an artificial intelligence model, wherein the artificial intelligence model is trained on a dataset comprising a plurality of dental scans representing unique dental structures to identify one or more undercuts; and
generating a digital model of a dental retainer based on the processed dental scan, wherein the digital model is optimized, through the artificial intelligence model, for the dental structure represented in the dental scan by eliminating one or more undercuts and establish borders for retainer fabrication.

2. The method of claim 1, further comprising the steps of fabricating the dental retainer based on the digital model using a manufacturing device.

3. The method of claim 1, wherein the artificial intelligence model comprises a machine learning model, a deep learning model, or a combination thereof.

4. The method of claim 1, wherein the unique dental structures comprises a variety of dental structures, dental conditions, or a combination thereof.

5. The method of claim 2, wherein the manufacturing device comprises a 3D printer.

6. The method of claim 1, further comprising the step of adjusting the digital model based on one or more corrections received from a user or a dental professional.

* * * * *